(12) United States Patent
Aikawa

(10) Patent No.: US 10,241,157 B2
(45) Date of Patent: Mar. 26, 2019

(54) DIFFERENTIAL TRANSFORMER-BASED PERMEABILITY SENSOR THAT DETECTS MAGNETIC SUBSTANCE

(71) Applicant: KYOCERA Document Solutions Inc., Osaka (JP)

(72) Inventor: Yukihiro Aikawa, Osaka (JP)

(73) Assignee: KYOCERA Document Solutions Inc., Tamatsukuri, Chuo-ku, Osaka (JP)

( * ) Notice: Subject to any disclaimer, the term of this patent is extended or adjusted under 35 U.S.C. 154(b) by 21 days.

(21) Appl. No.: 15/805,565

(22) Filed: Nov. 7, 2017

(65) Prior Publication Data

US 2018/0136290 A1    May 17, 2018

(30) Foreign Application Priority Data

Nov. 11, 2016   (JP) .................. 2016-220884

(51) Int. Cl.
   *G01R 33/00*   (2006.01)
   *G01N 27/72*   (2006.01)
   *G01R 33/12*   (2006.01)

(52) U.S. Cl.
   CPC ......... *G01R 33/0035* (2013.01); *G01N 27/72* (2013.01); *G01R 33/1223* (2013.01)

(58) Field of Classification Search
   CPC . G01R 33/1223; G01R 33/3873; G01N 27/72
   See application file for complete search history.

(56) References Cited

U.S. PATENT DOCUMENTS

| 8,994,367 B2 | 3/2015 | Aikawa | |
| 2008/0181642 A1* | 7/2008 | Kishi | G03G 15/2042 399/69 |
| 2010/0073832 A1* | 3/2010 | Chung | H02H 1/0015 361/42 |
| 2013/0099778 A1 | 4/2013 | Aikawa | |
| 2015/0277280 A1* | 10/2015 | Aikawa | G01N 27/72 324/228 |

FOREIGN PATENT DOCUMENTS

| JP | 2001-165910 A | 6/2001 |
| JP | 2013-101103 A | 5/2013 |

* cited by examiner

*Primary Examiner* — Giovanni Astacio-Oquendo
*Assistant Examiner* — Alvaro E Fortich
(74) *Attorney, Agent, or Firm* — IP Business Solutions, LLC

(57) ABSTRACT

A differential transformer-based permeability sensor includes a substrate including an insulation layer and a wiring layer stacked on each other, a first drive coil, a first induction coil, a second drive coil, a second induction coil, and a adjuster coil, all flatly formed on the wiring layer, a closed circuit including the adjuster coil and a current regulation element connected in parallel to ends of the adjuster coil, and an oscillation circuit. A circuit constituent is formed in which an oscillation signal of the oscillation circuit is provided to each of the drive coils, so that an induction current flows through the first induction coil, the second induction coil, and the adjuster coil, and a difference between the induction current of the first induction coil and that of the second induction coil is outputted. The induction current of the adjuster coil is adjusted according to resistance of a variable resistor.

10 Claims, 4 Drawing Sheets

DIFFERENTIAL TRANSFORMER-BASED PERMEABILITY SENSOR THAT DETECTS MAGNETIC SUBSTANCE

INCORPORATION BY REFERENCE

This application claims priority to Japanese Patent Application No. 2016-220884 filed on Nov. 11, 2016, the entire contents of which are incorporated by reference herein.

BACKGROUND

The present disclosure relates to a differential transformer-based permeability sensor that detects a magnetic substance, and more particularly to a technique to adjust a sensor.

In an image forming apparatus that utilizes electrophotography, for example, a differential transformer-based permeability sensor is employed to detect toner concentration and a residual amount of magnetic toner in a two-component developer, or whether the toner is still available. The differential transformer-based permeability sensor includes a plurality of coils, and in many cases the coils are formed in a helical shape on a substrate or a multilayer substrate, thus to have a minimized thickness.

The coil formed on a substrate or a multilayer substrate may produce an error in an output of the sensor owing to a dimensional error in the manufacturing process, and therefore the sensor has to be adjusted. For such adjustment, for example, the wire constituting the outermost circumference of the helical coil is branched into a plurality of branch lines, such that an amount of magnetic flux in each of the branch lines differs from each other, and one of the branch lines is selected.

SUMMARY

The disclosure proposes further improvement of the foregoing technique.

In an aspect, the disclosure provides a differential transformer-based permeability sensor including a substrate, a first drive coil, a first induction coil, a second drive coil, a second induction coil, an adjuster coil, a closed circuit, and an oscillation circuit.

The substrate includes an insulation layer and a wiring layer stacked on each other.

The first drive coil is a flat coil formed on the wiring layer.

The first induction coil, the second drive coil, the second induction coil, and the adjuster coil are flat coils.

The closed circuit includes the adjuster coil and a current regulation element connected in parallel to ends of the adjuster coil.

The oscillation circuit outputs an oscillation signal.

The first drive coil, the first induction coil, and the adjuster coil are concentrically arranged with respect to each other, and the second drive coil and the second induction coil are concentrically arranged with respect to each other.

A circuit constituent is formed in which the oscillation signal of the oscillation circuit is provided to the first drive coil and the second drive coil, so that an induction current flows through each of the first induction coil, the second induction coil, and the adjuster coil, and a difference between the induction current of the first induction coil and the induction current of the second induction coil is outputted.

The current regulation element adjusts the induction current flowing through the adjuster coil.

DETAILED DESCRIPTION

Hereafter, a differential transformer-based permeability sensor according to an embodiment of the disclosure will be described, with reference to the drawings.

Figure 1:
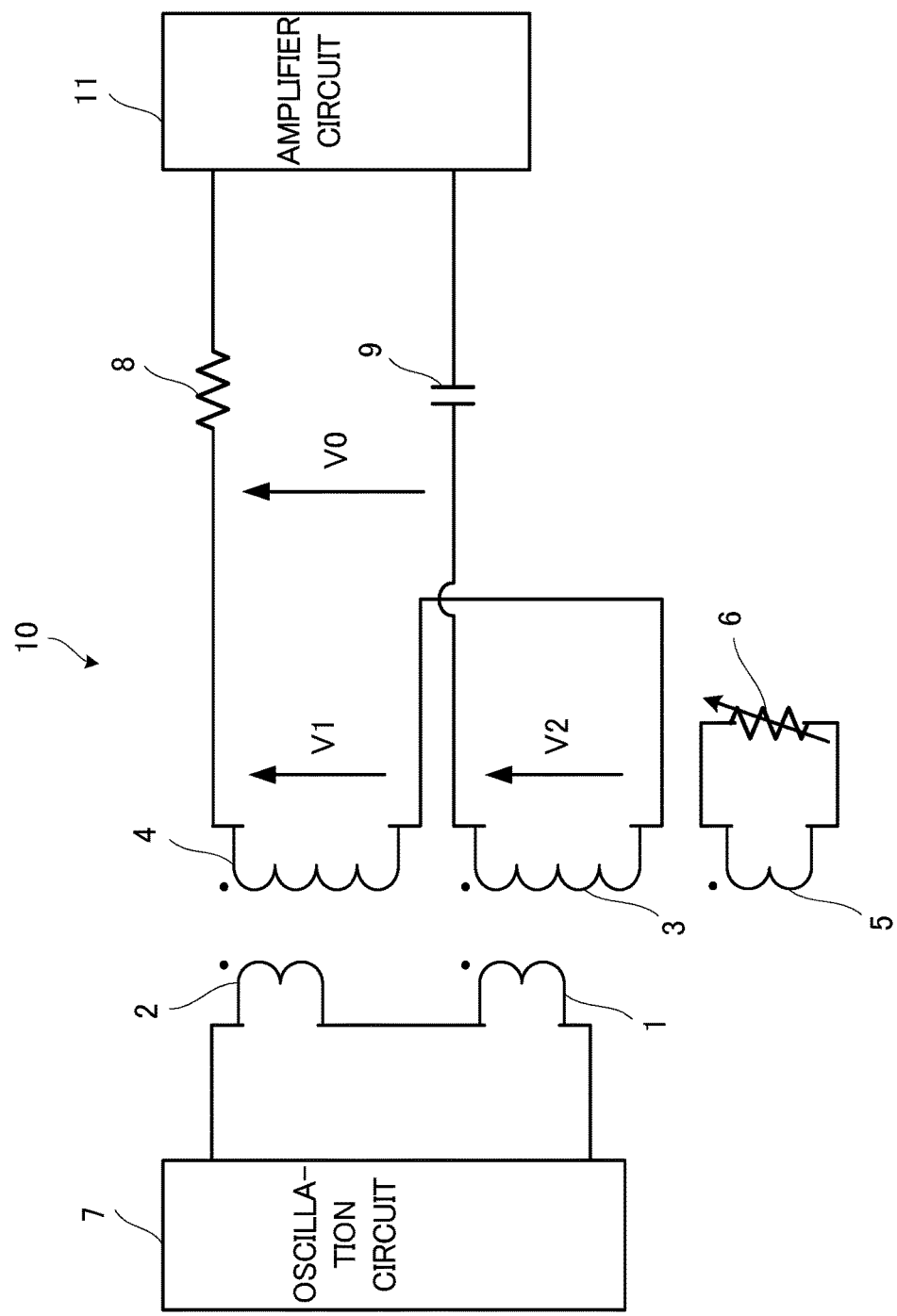
FIG. 1 is a block diagram of a differential transformer-based permeability sensor according to an embodiment of the disclosure.

FIG. 1 is a block diagram of the differential transformer-based permeability sensor according to the embodiment of the disclosure. The differential transformer-based permeability sensor 10 according to this embodiment is employed, for example, in a developing unit of an image forming apparatus that utilizes electrophotography, and serves to detect toner concentration and a residual amount of magnetic toner in a two-component developer in the developing unit, or whether the toner is still available.

As shown in FIG. 1, the differential transformer-based permeability sensor 10 includes a detection-side drive coil 1 (first drive coil in Claims), a reference-side drive coil 2 (second drive coil in Claims), a detection coil 3 (first induction coil in Claims), a reference coil 4 (second induction coil in Claims), an adjuster coil 5, a variable resistor 6 (current regulation element in Claims), an oscillation circuit 7, a resistor 8, a capacitor 9, and an amplifier circuit 11.

The oscillation circuit 7 generates a high-frequency drive current, and outputs the drive current to the detection-side drive coil 1 and the reference-side drive coil 2. The detection-side drive coil 1 and the reference-side drive coil 2 are connected in series, and each generate a magnetic flux according to the high-frequency drive current. In this embodiment, the polarity of the detection-side drive coil 1 and the polarity of the reference-side drive coil 2 are set such that the respective magnetic fluxes are oriented in the same direction.

The detection coil 3 is magnetically coupled with the detection-side drive coil 1, and hence an induction current based on the magnetic flux of the detection-side drive coil 1 is generated on the detection coil 3. Likewise, the reference coil 4 is magnetically coupled with the reference-side drive coil 2, and hence an induction current based on the magnetic flux of the reference-side drive coil 2 is generated on the reference coil 4. In this embodiment, the polarity of the detection coil 3 and the polarity of the reference coil 4, as well as the wiring pattern of the detection coil 3 and the reference coil 4, are arranged such that the respective induction currents cancel each other. Accordingly, a differential voltage V0, in other words a difference between the electromotive force (hereinafter, EMF) V1 of the reference coil 4 and the EMF V2 of the detection coil 3, is generated.

The detection coil 3 is connected to the amplifier circuit 11 via the capacitor 9, and the reference coil 4 is connected to the amplifier circuit 11 via the resistor 8. The resistor 8 is connected to the base of a bipolar transistor in the amplifier circuit 11, to be used to determine the amplification factor of the amplifier circuit 11.

The capacitor 9 cuts a DC component of the differential voltage V0. Accordingly, the amplifier circuit 11 receives only an AC component of the differential voltage V0.

The adjuster coil 5 is magnetically coupled with the detection-side drive coil 1, together with the detection coil 3. The adjuster coil 5 generates an induction current according to the magnetic flux of the detection-side drive coil 1. The variable resistor 6 is connected in parallel to the ends of the adjuster coil 5, so as to constitute a closed circuit composed of the adjuster coil 5 and the variable resistor 6. With the variable resistor 6, the amount of the induction current flowing through the adjuster coil 5 and the variable resistor 6 can be increased or decreased. In other words, the induction current of the adjuster coil 5 is adjusted according to the resistance of the variable resistor 6.

Now, since the detection coil 3 and the adjuster coil 5 are magnetically coupled with the detection-side drive coil 1, when the amount of the induction current flowing through the adjuster coil 5 is increased by reducing the resistance of the variable resistor 6, the amount of the induction current flowing through the detection coil 3 is decreased. Conversely, when the amount of the induction current flowing through the adjuster coil 5 is decreased by increasing the resistance of the variable resistor 6, the amount of the induction current flowing through the detection coil 3 is increased. The EMF V2 of the detection coil 3 can thus be adjusted by increasing or decreasing the resistance of the variable resistor 6.

In the differential transformer-based permeability sensor 10 configured as above, the detection coil 3 is located closer to the toner in the developing unit, than is the reference coil 4. When the toner is undetected, the amount of the induction current flowing through the adjuster coil 5 is adjusted by increasing or decreasing the resistance of the variable resistor 6, so as to make the EMF V2 of the detection coil 3 equal to the EMF V1 of the reference coil 4, and thus the differential voltage V0 is preset to "0". Accordingly, the output of the amplifier circuit 11 becomes "0".

When the detection coil 3 detects the toner after the differential voltage V0 is preset to "0", the induction current of the detection coil 3 is increased so as to increase the EMF V2 of the detection coil 3, and the differential voltage V0 fluctuates, so that the AC component of the differential voltage V0 is amplified by the amplifier circuit 11 and outputted therefrom. Thus, the toner concentration and the residual amount of the magnetic toner in the two-component developer, or whether the toner is present, can be detected on the basis of the output from the amplifier circuit 11.

However, in the configuration including the adjuster coil 5, the amount of the induction current of the detection coil 3 always becomes lower than that of the reference coil 4, in the case where the same coils are employed as the detection coil 3 and the reference coil 4. Accordingly, the EMF V2 of the detection coil 3 is unable to be equal to the EMF V1 of the reference coil 4, despite adjusting the amount of the induction current flowing through the adjuster coil 5 by increasing or decreasing the resistance of the variable resistor 6, and hence the differential voltage V0 is unable to be set to "0".

In this embodiment, therefore, the number of turns of the reference coil 4 is fewer than that of the detection coil 3. Alternatively, the distance between the reference-side drive coil 2 and the reference coil 4 is made longer than the distance between the detection-side drive coil 1 and the detection coil 3, in other words the magnetic coupling coefficient between the reference-side drive coil 2 and the reference coil 4 is set to be smaller than the magnetic coupling coefficient between the detection-side drive coil 1 and the detection coil 3. The mentioned arrangement allows, when the toner is undetected, the amount of the induction current of the detection coil 3 to be increased or decreased in a range over or under the amount of the induction current of the reference coil 4, by increasing or decreasing the resistance of the variable resistor 6 thereby adjusting the amount of the induction current flowing through the adjuster coil 5. Therefore, the EMF V2 of the detection coil 3 can be made equal to the EMF V1 of the reference coil 4, to set the differential voltage V0 to "0".

In addition, since the resistance of the variable resistor 6 varies successively and smoothly, the EMF V2 of the detection coil 3 can be made accurately equal to the EMF V1 of the reference coil 4, to thereby set the differential voltage V0 to "0" with high accuracy.

Hereunder, specific configurations of the detection-side drive coil 1, the reference-side drive coil 2, the detection coil 3, the reference coil 4, and the adjuster coil 5 in the differential transformer-based permeability sensor 10 will be described.

Figure 2:
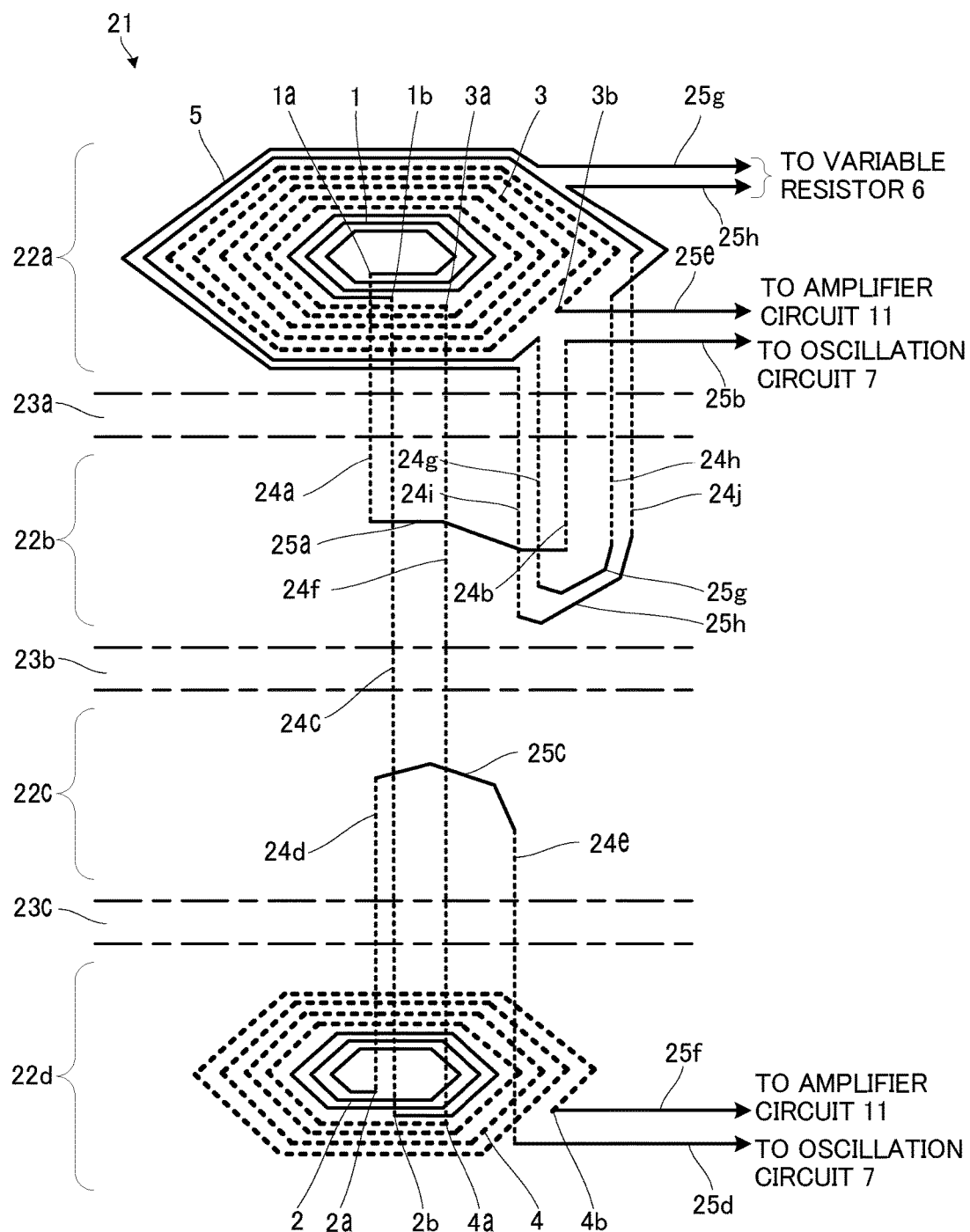
FIG. 2 is a perspective view showing a multilayer substrate on which a plurality of coils, constituting the differential transformer-based permeability sensor shown in FIG. 1, is formed.

FIG. 2 is a perspective view showing a multilayer substrate 21 on which the detection-side drive coil 1, the reference-side drive coil 2, the detection coil 3, the reference coil 4, and the adjuster coil 5 are formed. As shown in FIG. 2, the multilayer substrate 21 includes a first wiring layer 22a, a second wiring layer 22b, a third wiring layer 22c, a fourth wiring layer 22d, a first insulation layer 23a, a second insulation layer 23b, and a third insulation layer 23c, which are stacked on each other. The first to the third insulation layers 23a to 23c are interposed between the first to the fourth wiring layers 22a to 22d, so that the first to the fourth wiring layers 22a to 22d are insulated from each other.

On the first wiring layer 22a, the detection-side drive coil 1, the detection coil 3, and the adjuster coil 5, all of which are flat, are arranged in a concentric pattern, and the mentioned coils 1, 3, and 5 are magnetically coupled. The winding direction of the detection-side drive coil 1 is counterclockwise from the inner portion toward the outer portion of the coil 1, in a view from above. The winding direction of the detection coil 3 and the adjuster coil 5 is clockwise from the inner portion toward the outer portion of the coils 3 and 5, in a view from above.

On the fourth wiring layer 22d, the reference-side drive coil 2 and the reference coil 4, which are both flat, are arranged in a concentric pattern, and the coils 2 and 4 are magnetically coupled. The winding direction of the reference-side drive coil 2 and the reference coil 4 is clockwise from the inner portion toward the outer portion of the coils 3 and 5, in a view from above.

The inner end 1a of the detection-side drive coil 1 is connected to a conductive pattern 25a of the second wiring layer 22b, through a via 24a penetrating through the first insulation layer 23a. The conductive pattern 25a is connected to a conductive pattern 25b of the first wiring layer 22a, through a via 24b in the first insulation layer 23a, and the conductive pattern 25b is connected to the oscillation circuit 7. Accordingly, the inner end 1a of the detection-side drive coil 1 is connected to the oscillation circuit 7, through the via 24a, the conductive pattern 25a, the via 24b, and the conductive pattern 25b.

The outer end 1b of the detection-side drive coil 1 is connected to the outer end 2b of the reference-side drive coil 2, through a via 24c penetrating through the first to the third insulation layers 23a to 23c and the second and third wiring layers 22b and 22c. Accordingly, the detection-side drive coil 1 and the reference-side drive coil 2 are connected in series.

The inner end 2a of the reference-side drive coil 2 is connected to a conductive pattern 25c of the third wiring layer 22c, through a via 24d penetrating through the third insulation layer 23c. In addition, the conductive pattern 25c is connected to a conductive pattern 25d of the fourth wiring layer 22d through a via 24e in the third insulation layer 23c, and the conductive pattern 25d is connected to the oscillation circuit 7. Accordingly, the inner end 2a of the reference-side drive coil 2 is connected to the oscillation circuit 7, through the via 24d, the conductive pattern 25c, the via 24e, and the conductive pattern 25d.

The inner end 3a of the detection coil 3 is connected to the inner end 4a of the reference coil 4, through a via 24f penetrating through the first to the third insulation layers 23a to 23c and the second and third wiring layers 22b and 22c. The outer end 3b of the detection coil 3 is connected to a conductive pattern 25e of the first wiring layer 22a, and then to the capacitor 9 through the conductive pattern 25e. The outer end 4b of the reference coil 4 is connected to a conductive pattern 25f of the fourth wiring layer 22a, and then to the resistor 8 through the conductive pattern 25f.

The adjuster coil 5 receives electricity through two vias 24g and 24h penetrating through the first insulation layer 23a, and a conductive pattern 25g of the second wiring layer 22b, and also through other two vias 24i and 24j penetrating through the first insulation layer 23a and another conductive pattern 25h of the second wiring layer 22b. Accordingly, the first wiring layer 22a includes a vacant space that allows the conductive pattern 25e to be led out without contacting the adjuster coil 5.

The respective ends of the adjuster coil 5 are connected to the two conductive patterns 25g and 25h of the first wiring layer 22a, and then to the variable resistor 6, through the conductive patterns 25g and 25h.

The multilayer substrate 21 configured as above constitutes the circuit shown in FIG. 1. The winding direction of the detection-side drive coil 1, the reference-side drive coil 2, the detection coil 3, the reference coil 4, and the adjuster coil 5 shown in FIG. 2 may be changed, depending on the connection of the wiring to each of the coils 1 to 5. In addition, it will be assumed that the inner surface of the vias 24a to 24j is plated, so that the vias 24a to 24j are electrically conductive.

Now, the detection-side drive coil 1, the reference-side drive coil 2, the detection coil 3, and the reference coil 4 formed on the multilayer substrate 21 may suffer a dimensional error through the manufacturing process, and such an error may provoke an error of the output of the differential transformer-based permeability sensor 10.

In this embodiment, as described above, the amount of the induction current flowing through the adjuster coil 5 is made to vary successively and smoothly, by increasing or decreasing the resistance of the variable resistor 6, when the toner is undetected, to thereby make the EMF V2 of the detection coil 3 accurately equal to the EMF V1 of the reference coil 4, thus to set the differential voltage V0 to "0" with high accuracy. Therefore, the error of the output can be corrected.

In addition, as described above, the number of turns of the reference coil 4 is made fewer than that of the detection coil 3, or the magnetic coupling coefficient between the reference-side drive coil 2 and the reference coil 4 is set to be smaller than the magnetic coupling coefficient between the detection-side drive coil 1 and the detection coil 3, by making the distance between the reference-side drive coil 2 and the reference coil 4 longer than the distance between the detection-side drive coil 1 and the detection coil 3. Therefore, the differential voltage V0 can be set to "0" by increasing or decreasing the resistance of the variable resistor 6, when the toner is undetected.

Here, with the aforementioned adjustment method, in other words selecting one of the plurality of branch lines of the outermost circumference of the helical coil, the output of the sensor varies stepwise. Therefore, the output of the sensor is unable to be successively varied, to be adjusted with high accuracy.

In contrast, the differential transformer-based permeability sensor 10 according to this embodiment is capable of successively changing the output of the sensor, to adjust with high accuracy.

Although the adjuster coil 5 is magnetically coupled with the detection-side drive coil 1 in this embodiment, the adjuster coil 5 may be magnetically coupled with the reference-side drive coil 2, thus to connect the variable resistor 6 in parallel to the adjuster coil 5. In this case, the reference-side drive coil 2 corresponds to the first drive coil in the disclosure, the detection-side drive coil 1 corresponds to the second drive coil in the disclosure, the reference coil 4 corresponds to the first induction coil in the disclosure, and the detection coil 3 corresponds to the second induction coil in the disclosure. Alternatively, the adjuster coil 5 may be located on the fourth wiring layer 22d of the multilayer substrate 21, on the outer side of the reference coil 4. Further, the number of turns of the detection coil 3 may be made fewer than that of the reference coil 4, or the magnetic coupling coefficient between the detection-side drive coil 1 and the detection coil 3 may be set to be smaller than the magnetic coupling coefficient between the reference-side drive coil 2 and the reference coil 4. Then the differential voltage V0 may be set to "0" by increasing or decreasing the resistance of the variable resistor 6, when the toner is undetected.

First Variation

Figure 3:
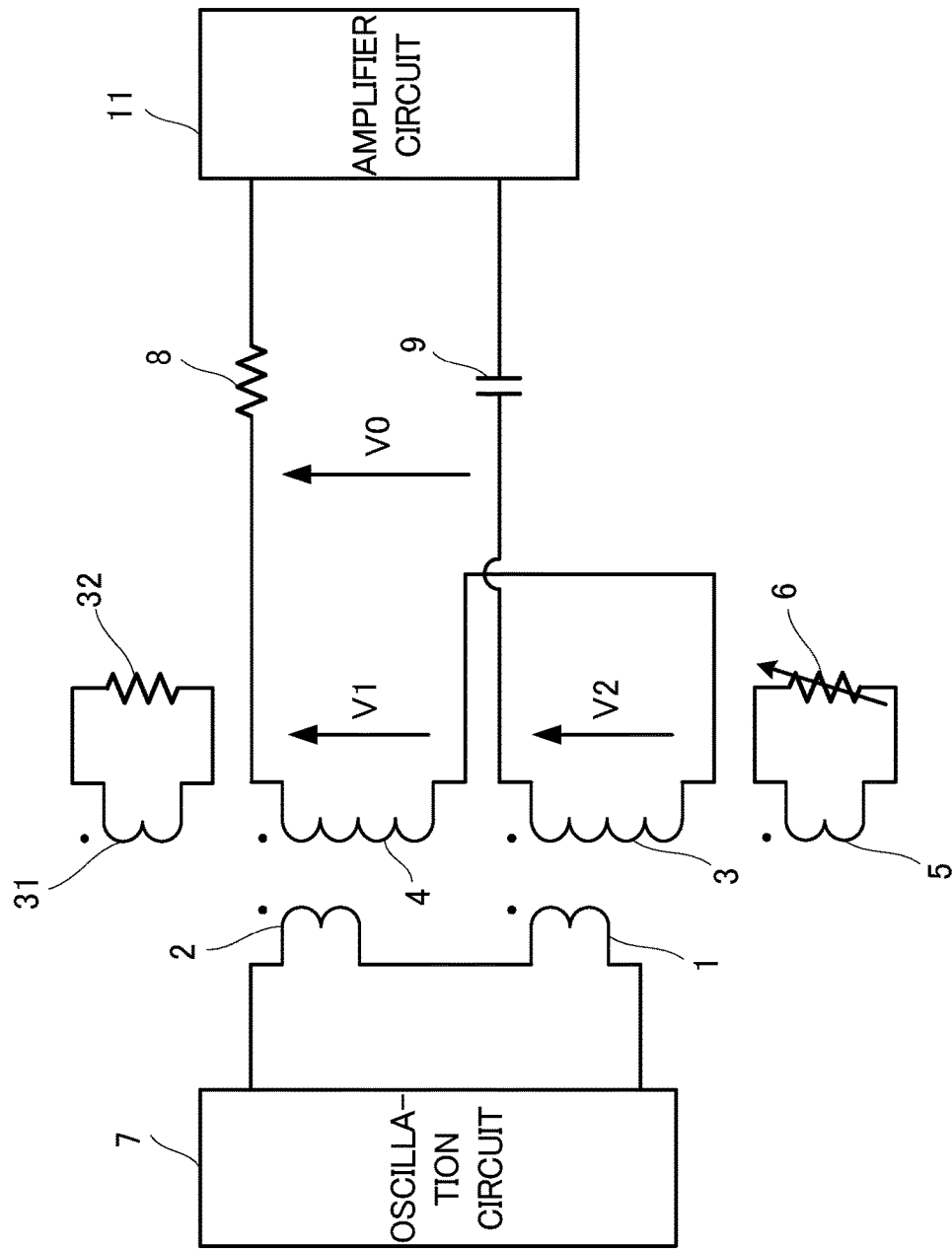
FIG. 3 is a block diagram of a variation of the differential transformer-based permeability sensor.

In a first variation, instead of reducing the number of turns of the reference coil 4 from that of the detection coil 3, or setting the magnetic coupling coefficient between the reference-side drive coil 2 and the reference coil 4 to be smaller than the magnetic coupling coefficient between the detection-side drive coil 1 and the detection coil 3, as in the foregoing embodiment, a closed circuit composed of a correction coil 31 and a fixed resistor 32, connected in parallel to the ends of the correction coil 31, is provided as shown in FIG. 3, so that the correction coil 31 is magnetically coupled with the reference-side drive coil 2, together with the reference coil 4.

The correction coil 31 generates an induction current according to the magnetic flux of the reference-side drive coil 2, and hence the induction current flowing through the reference coil 4 is decreased, compared with the case where the correction coil 31 is not provided. Therefore, the induction current of the detection coil 3 is decreased by the adjuster coil 5, and also the induction current of the reference coil 4 is decreased, owing to the presence of the correction coil 31.

For example, the magnetic coupling coefficient and the number of turns of the detection-side drive coil 1, the detection coil 3, and the adjuster coil 5 may be set to be equal of the magnetic coupling coefficient and the number of turns of the reference-side drive coil 2, the reference coil 4, and the correction coil 31, so that the resistance of the fixed resistor 32 falls within the resistance range of the variable resistor 6. More specifically, the resistance range of the variable resistor 6 may be set to 10Ω to 1KΩ, and the resistance of the fixed resistor 32 may be set to 100Ω. Such an arrangement allows the amount of the induction current of the detection coil 3 to be increased or decreased in a range over or under the amount of the induction current of the reference coil 4, by increasing or decreasing the resistance of the variable resistor 6 thereby adjusting the amount of the induction current flowing through the adjuster coil 5. Consequently, the EMF V2 of the detection coil 3 can be set to be equal to the EMF V1 of the reference coil 4, and thus the differential voltage V0 can be set to "0".

Although the adjuster coil 5 is magnetically coupled with the detection-side drive coil 1, and the correction coil 31 is magnetically coupled with the reference-side drive coil 2 in the first variation, the adjuster coil 5 may instead by magnetically coupled with the reference-side drive coil 2, and the correction coil 31 may be magnetically coupled with the detection-side drive coil 1. Then the variable resistor 6 may be connected in parallel to the adjuster coil 5, and the fixed resistor 32 may be connected in parallel to the correction coil 31. Such an arrangement also enables the differential voltage V0 to be set to "0", by increasing or decreasing the resistance of the variable resistor 6, when the toner is undetected.

Second Variation

Figure 4:
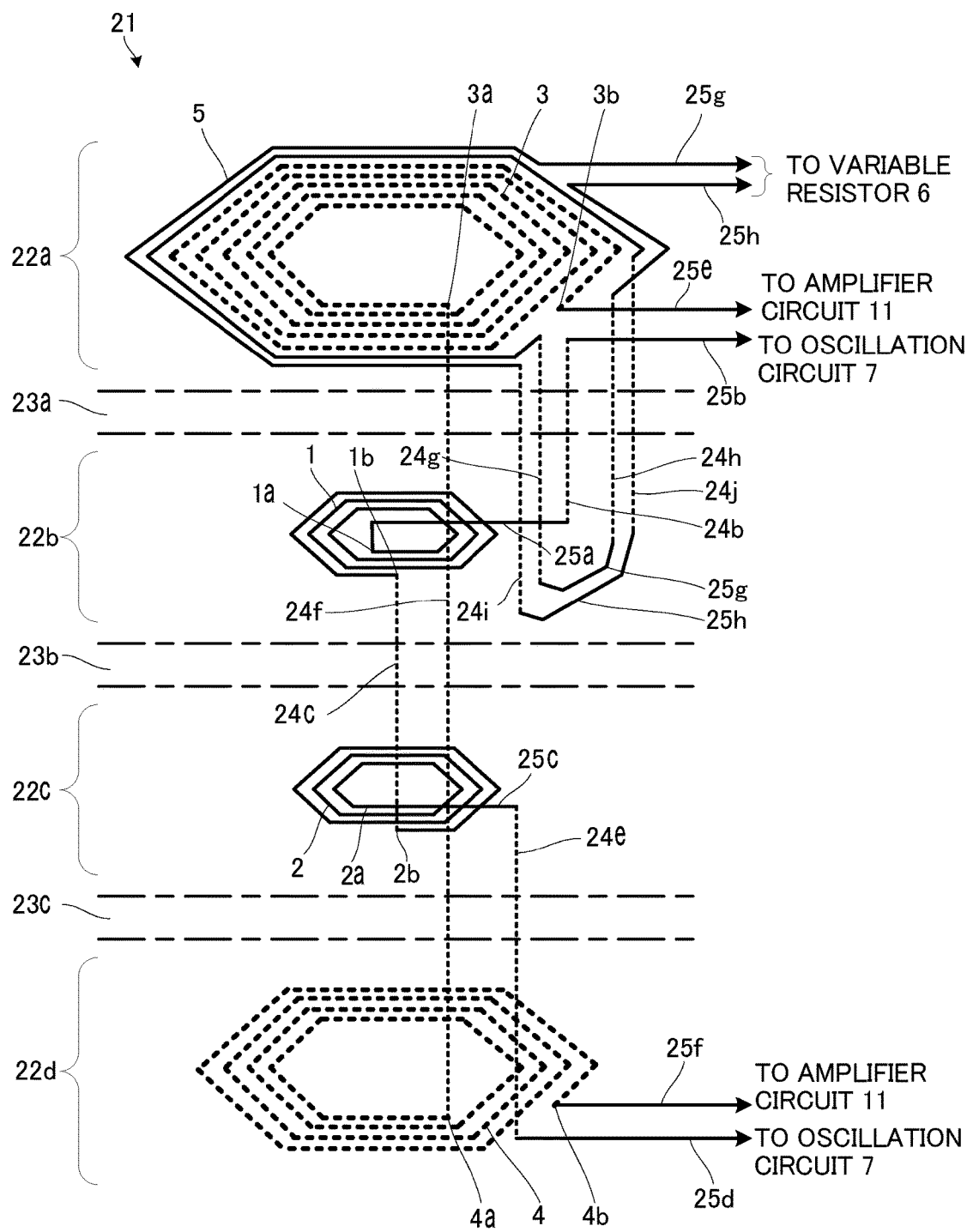
FIG. 4 is a perspective view showing a variation of the multilayer substrate.

In a second variation, as shown in FIG. 4, the detection coil 3 and the adjuster coil 5 are provided on the first wiring layer 22*a*, and the detection-side drive coil 1 is provided on the second wiring layer 22*b*. In addition, the reference coil 4 is provided on the fourth wiring layer 22*d*, and the reference-side drive coil 2 is provided on the third wiring layer 22*c*. Further, the vias 24*c*, 24*e*, and 24*f*, and the conductive patterns 25*a* and 25*c* are provided to connect the detection-side drive coil 1, the reference-side drive coil 2, the reference coil 4, and the adjuster coil 5, so as to constitute the circuit shown in FIG. 1.

The mentioned configuration also allows the detection coil 3 and the adjuster coil 5 to be magnetically coupled with the detection-side drive coil 1, and the reference coil 4 to be magnetically coupled with the reference-side drive coil 2, and therefore the same advantageous effects as those provided by the foregoing embodiment can be attained.

Further, the detection-side drive coil 1, the reference-side drive coil 2, the detection coil 3, the reference coil 4, and the adjuster coil 5 may all be formed on the same wiring layer, such that the detection-side drive coil 1, the detection coil 3, and the adjuster coil 5 are spaced from the reference-side drive coil 2 and the reference coil 4 on the wiring layer. In this case also, the same circuit as shown in FIG. 1 can be obtained.

Although the detection-side drive coil 1, the reference-side drive coil 2, the detection coil 3, the reference coil 4, and the adjuster coil 5 are helical coils in the embodiment and variations, these coils may each be a single-loop coil. The loop coil may be opened or closed, and the plan-view shape of the coil may be circular or polygonal.

Although the variable resistor exemplifies the current regulation element in the foregoing embodiment, a device such as a transistor, including an FET, may be connected in parallel to the ends of the adjuster coil 5, in place of the variable resistor, and a current or voltage may be applied from outside to the device, so as to increase or decrease the induction current flowing through the adjuster coil 5.

Further, the configurations and arrangements described with reference to FIG. 1 to FIG. 4 are merely an embodiment of the disclosure, and in no way intended to limit the configurations and arrangements of the disclosure.

While the present disclosure has been described in detail with reference to the embodiments thereof, it would be apparent to those skilled in the art the various changes and modifications may be made therein within the scope defined by the appended claims.

What is claimed is:

1. A differential transformer-based permeability sensor comprising:
   a substrate including an insulation layer and a wiring layer stacked on each other;
   a flat first drive coil, a flat first induction coil, a flat second drive coil, a flat second induction coil, and a flat adjuster coil formed on the wiring layer;
   a closed circuit including the adjuster coil and a current regulation element connected in parallel to ends of the adjuster coil; and
   an oscillation circuit that outputs an oscillation signal,
   wherein the first drive coil, the first induction coil, and the adjuster coil are concentrically arranged with respect to each other, and the second drive coil and the second induction coil are concentrically arranged with respect to each other,
   a circuit constituent is formed in which the oscillation signal of the oscillation circuit is provided to the first drive coil and the second drive coil, so that an induction current flows through each of the first induction coil, the second induction coil, and the adjuster coil, and a difference between the induction current of the first induction coil and the induction current of the second induction coil is outputted, and
   the adjuster coil is provided with the current regulation element that adjusts the induction current flowing through the adjuster coil.

2. The differential transformer-based permeability sensor according to claim 1,
   wherein a number of turns of the second induction coil is fewer than a number of turns of the first induction coil, concentrically arranged with respect to the adjuster coil.

3. The differential transformer-based permeability sensor according to claim 1,
   wherein a magnetic coupling coefficient between the second induction coil and the second drive coil is smaller than a magnetic coupling coefficient between the first induction coil and the first drive coil, concentrically arranged with respect to the adjuster coil.

4. The differential transformer-based permeability sensor according to claim 1, further comprising:
   a closed circuit including a correction coil concentrically arranged with respect to the second drive coil and the second induction coil, and a fixed resistor connected in parallel to ends of the correction coil,
   wherein an induction current flows through the correction coil, when the oscillation signal of the oscillation circuit is provided to the second drive coil.

5. The differential transformer-based permeability sensor according to claim 1,
   wherein the first induction coil is located closer to a magnetic substance to be detected, than is the second induction coil.

6. The differential transformer-based permeability sensor according to claim 1, wherein the second induction coil is located closer to a magnetic substance to be detected, than is the first induction coil.

7. The differential transformer-based permeability sensor according to claim 1, wherein the first drive coil, the first induction coil, and the adjuster coil are spaced from the second drive coil and the second induction coil, on the wiring layer of the substrate.

8. The differential transformer-based permeability sensor according to claim 1, wherein the substrate includes two wiring layers stacked with the insulation layer interposed therebetween, the first drive coil, the first induction coil, and the adjuster coil are provided on one side of the wiring layers, and the second drive coil and the second induction coil are provided on an another side of the wiring layer.

9. The differential transformer-based permeability sensor according to claim 1, wherein the substrate includes a first wiring layer, a second wiring layer, a third wiring layer, and a fourth wiring layer, sequentially stacked via a corresponding insulation layer, the first induction coil and the adjuster coil are provided on the first wiring layer, the first drive coil is provided on the second wiring layer, the second drive coil is provided on the third wiring layer, and the second induction coil is provided on the fourth wiring layer.

10. The differential transformer-based permeability sensor according to claim 4, wherein a magnetic coupling coefficient and a number of turns of the first drive coil, the first induction coil, and the adjuster coil are equal to a magnetic coupling coefficient and a number of turns of the second drive coil, the second induction coil, and the correction coil, and a resistance of the fixed resistor falls within a resistance range of the current regulation element.

* * * * *